United States Patent
Akhtari

(10) Patent No.: US 9,272,055 B2
(45) Date of Patent: Mar. 1, 2016

(54) FUNCTIONALIZED MAGNETIC NANOPARTICLES AND USE IN IMAGING AMYLOID DEPOSITS AND NEUROFIBRILLARY TANGLES

(75) Inventor: Massoud Akhtari, Pasadena, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/007,298

(22) PCT Filed: Apr. 4, 2012

(86) PCT No.: PCT/US2012/032100
§ 371 (c)(1),
(2), (4) Date: Dec. 9, 2013

(87) PCT Pub. No.: WO2012/145169
PCT Pub. Date: Oct. 26, 2012

(65) Prior Publication Data
US 2014/0140932 A1      May 22, 2014

Related U.S. Application Data

(60) Provisional application No. 61/477,958, filed on Apr. 21, 2011.

(51) Int. Cl.
| | |
|---|---|
| *A61K 31/44* | (2006.01) |
| *A61K 31/277* | (2006.01) |
| *A61K 49/10* | (2006.01) |
| *A61K 31/4745* | (2006.01) |
| *A61K 31/132* | (2006.01) |
| *A61K 31/133* | (2006.01) |
| *A61K 31/136* | (2006.01) |
| *A61K 31/145* | (2006.01) |
| *A61K 31/167* | (2006.01) |
| *A61K 31/427* | (2006.01) |
| *A61K 31/428* | (2006.01) |
| *A61K 31/4439* | (2006.01) |
| *A61K 31/444* | (2006.01) |
| *A61K 31/472* | (2006.01) |
| *A61K 49/18* | (2006.01) |

(52) U.S. Cl.
CPC ............. *A61K 49/10* (2013.01); *A61K 31/132* (2013.01); *A61K 31/133* (2013.01); *A61K 31/136* (2013.01); *A61K 31/145* (2013.01); *A61K 31/167* (2013.01); *A61K 31/277* (2013.01); *A61K 31/427* (2013.01); *A61K 31/428* (2013.01); *A61K 31/44* (2013.01); *A61K 31/444* (2013.01); *A61K 31/4439* (2013.01); *A61K 31/472* (2013.01); *A61K 31/4745* (2013.01); *A61K 49/1833* (2013.01)

(58) Field of Classification Search
CPC ........... A61K 51/00; A61K 9/00; A61K 9/14; A61K 49/18; A61K 49/00; A61K 31/44; A61K 31/277; A61K 31/428
See application file for complete search history.

(56) References Cited

U.S. PATENT DOCUMENTS

| | | | |
|---|---|---|---|
| 5,411,730 A | 5/1995 | Kirpotin et al. | |
| 6,274,119 B1 * | 8/2001 | Barrio et al. | 424/1.81 |
| 6,534,039 B2 | 3/2003 | Hainfeld | |
| 6,548,264 B1 | 4/2003 | Tan et al. | |
| 6,767,635 B1 | 7/2004 | Bahr et al. | |
| 7,270,800 B2 | 9/2007 | Klunk et al. | |
| 8,349,293 B2 | 1/2013 | Corot | |
| 2005/0260126 A1 | 11/2005 | Kudo et al. | |
| 2006/0111288 A1 | 5/2006 | Cotter et al. | |
| 2008/0021077 A1 | 1/2008 | Klunk et al. | |
| 2008/0206146 A1 * | 8/2008 | Akhtari et al. | 424/9.3 |
| 2008/0299557 A1 | 12/2008 | Himmelreich et al. | |
| 2010/0098634 A1 | 4/2010 | Kolb et al. | |

FOREIGN PATENT DOCUMENTS

| | | |
|---|---|---|
| CN | 101544584 A | 9/2009 |
| FR | 2913886 A1 | 9/2008 |
| WO | 02/029441 A2 | 4/2002 |
| WO | WO 02/028441 A2 | 4/2002 |
| WO | 02/094191 A2 | 11/2002 |
| WO | 2006102377 | 9/2006 |
| WO | 2009123734 | 10/2009 |
| WO | 2010078370 | 7/2010 |

OTHER PUBLICATIONS

Agdeppa et al., "In vitro detection of (S)-naproxen and ibuprofen binding to plaques in the Alzheimer's brain using the positron emission tomography molecular imaging probe 2-(1-[6-[(2-[(18)F]fluoroethyl)(methyl)amino]-2-naphthyl]ethylidene)malononitrile",Neuroscience, 2003, 117(3):723-730.
Berry et al., "Functionalisation of magnetic nanoparticles for applications in biomedicine", J Phys D: Applied Physics, 2003, 36(13):R198-R206.
Dousset et al., "Comparison of ultrasmall particles of iron oxide (USPIO)-enhanced T2-weighted, conventional T2-weighted, and gadolinium-enhanced T1-weighted MR images in rats with experimental autoimmune encephalomyelitis", AJNR Am J Neuororadiol, 1999, 20(2):223-227.
Dousset et al., "In vivo macrophage activity imaging in the central nervous system detected by magnetic resonance", Magn Reson Med, 1999, 41(2):329-333.

(Continued)

*Primary Examiner* — Michael G Hartley
*Assistant Examiner* — Jagadishwar Samala
(74) *Attorney, Agent, or Firm* — Bozicevic, Field & Francis LLP; Paula A. Borden

(57) ABSTRACT

The present disclosure provides functionalized magnetic nanoparticles (MNPs) comprising a functional group that binds to β-amyloid deposits and/or neurofibrillary tangles. The present disclosure provides compositions comprising the functionalized MNPs, and methods of using the functionalized MNPs in imaging β-amyloid deposits and neurofibrillary tangles.

11 Claims, 8 Drawing Sheets

(56) References Cited

OTHER PUBLICATIONS

Dunning et al., "Superparamagnetic iron oxide-labeled Schwann cells and olfactory ensheathing cells can be traced in vivo by magnetic resonance imaging and retain functional properties after transplantation into the CNS", J Neurosci, 2004, 24(44):9799-9810.

Klunk; et al. "Imaging brain amyloid in Alzheimer's disease with Pittsburgh Compound-B", Ann Neurol (Mar. 2004), 55(3):306-319.

Lee et al. "Imaging of Alzheimer's disease", J. Neuroimaging, 2003,13(3):199-214.

McBain et al., "Magnetic nanoparticles for gene and drug delivery", Int J Nanomedicine, 2008, 3(2):169-180.

Moghimi et al., "Long-circulating and target-specific nanoparticles: theory to practice", Pharmacol Rev, 2001, 53 (2):283-318.

Pankhurst et al., "Applications of magnetic nanoparticles in biomedicine", J Phys D: Applied Physics, 2003, 36: R167-R181.

Puchtler; et al. "Brain amyloid can be shown by staining brain sections with thioflavin S or Congo red" J Histochem Cytochem, 1962,10:35.

Choi, et al.; "Preclinical Properties of $^{18}$F-AV-45: A PET Agent for Aβ Plaques in the Brain"; The Journal of Nuclear Medicine; vol. 50, No. 11, pp. 1887-1894 (Oct. 16, 2009).

Kung, et al.; "Binding of two potential imaging agents targeting amyloid plaques in postmortem brain tissues of patients with Alzheimer's disease"; Brain Research; vol. 1025, No. 1-2, pp. 98-105 (Oct. 29, 2004).

Zhang, et al.; "F-18 Polyethyleneglycol stilbenes as PET imaging agents targeting Aβ aggregates in the brain"; Nuclear Medicine and Biology; vol. 32, No. 8, pp. 799-809 (Nov. 1, 2005).

\* cited by examiner

FUNCTIONALIZED MAGNETIC NANOPARTICLES AND USE IN IMAGING AMYLOID DEPOSITS AND NEUROFIBRILLARY TANGLES

CROSS-REFERENCE

This application claims the benefit of U.S. Provisional Patent Application No. 61/477,958, filed Apr. 21, 2011, which application is incorporated herein by reference in its entirety.

BACKGROUND

Nanoparticles are very small particles typically ranging in size from as small as one nanometer to as large as several hundred nanometers in diameter. Their small size allows nanoparticles to be exploited to produce a variety of products such as dyes and pigments; aesthetic or functional coatings; tools for biological discovery, medical imaging, and therapeutics; magnetic recording media; quantum dots; and even uniform and nanosize semiconductors.

Amyloid deposits and neurofibrillary tangles (NFT, also known as paired helical filaments, PHF) are hallmarks of various diseases, including Alzheimer's disease (AD). There is a need in the art for methods of imaging amyloid deposits and NFT in brains of living individuals having or suspected of having AD.

LITERATURE

U.S. Pat. Nos. 6,548,264, and 6,767,635; Berry and Curtis (2003) *J. Phys. D: Applied Physics* 36:R198-R206; Pankhurst et al. (2003) *J. Phys. D: Applied Physics* 36:R167-R181; Dousset et al. (1999) *Am. J. Neuroradiol.* 20:223-227; Dunning et al. (2004) *J. Neurosci.* 24:9799-9810; Dousset et al. (1999) *Magnetic Resonance in Medicine* 41:329-333; Moghimi et al. (2001) *Pharmacol. Rev.* 53:283-318; Puchtler et al. (1962) *J. Histochem. Cytochem.* 10:35; Klunk et al. (2004) *Annals Neural.* 55:306; U.S. Pat. No. 7,270,800; U.S. Pat. No. 6,274,119; Agdeppa et al. (2003) *Neurosci.* 117:723; U.S. Pat. No. 5,411,730; U.S. Pat. No. 6,534,039; U.S. Patent Publication No. 2008/0206146; WO 2006/102377; Lee et al. (2003) *J. Neuroimaging* 13:199.

SUMMARY OF THE INVENTION

The present disclosure provides functionalized magnetic nanoparticles (MNPs) comprising a functional group that binds to β-amyloid deposits and/or NFT (PHF). The present disclosure provides compositions comprising the functionalized MNPs, and methods of using the functionalized MNPs in imaging β-amyloid deposits and/or NFT (PHF).

DEFINITIONS

Figure 1:
FIGS. 1A and 1B depict magnetic resonance (MR) images of a naïve rat brain.
Figure 1:
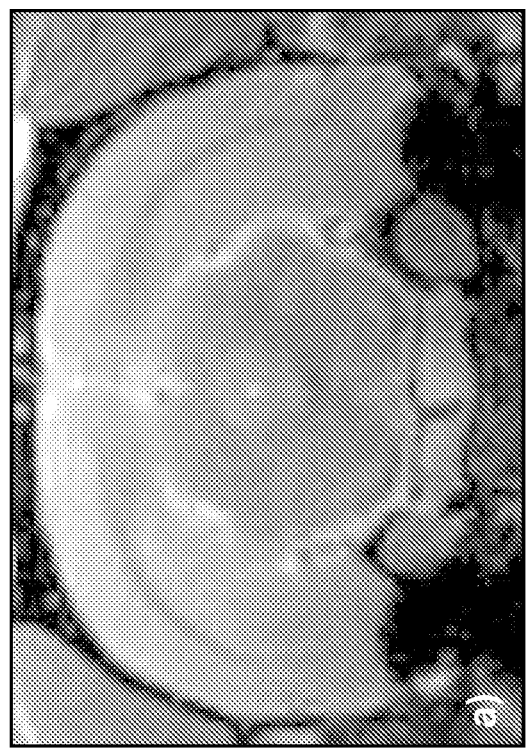
Figure 2:
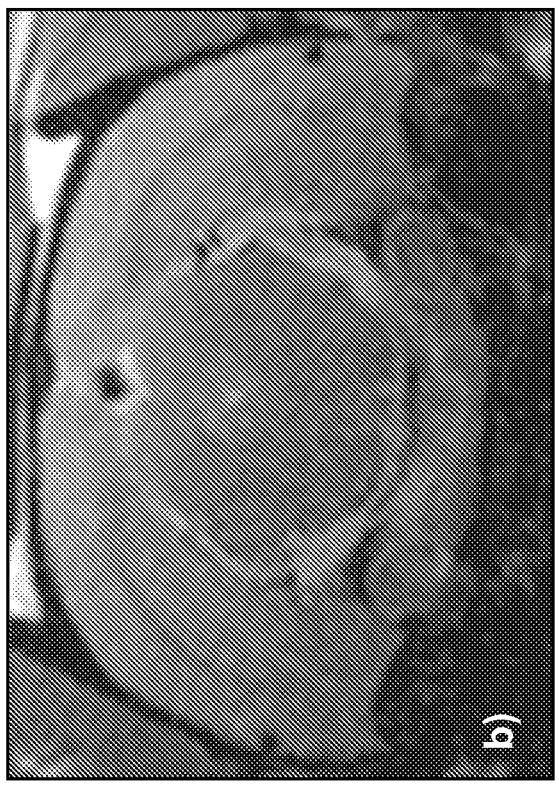
FIGS. 2A and 2B depict MR images of the brain of a rat model of Alzheimer's disease.
Figure 2:
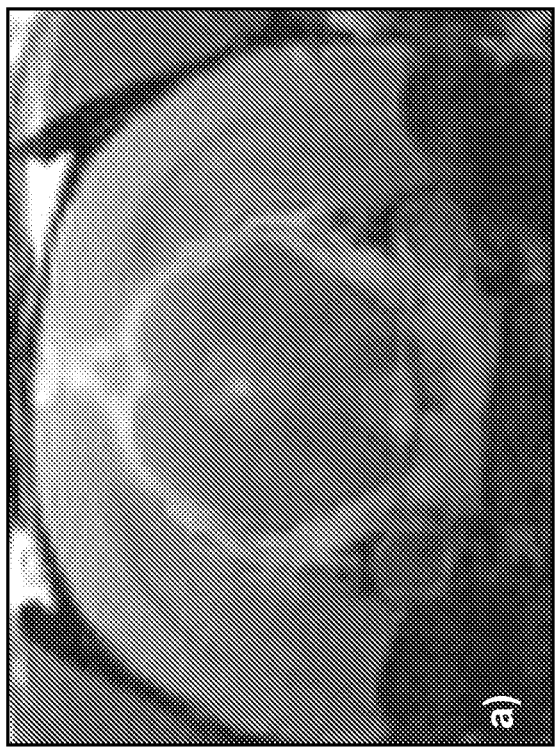
Figure 3:
FIGS. 3A and 3B depict MR images of the brain of a second rat that is a rat model of Alzheimer's disease.
Figure 3:
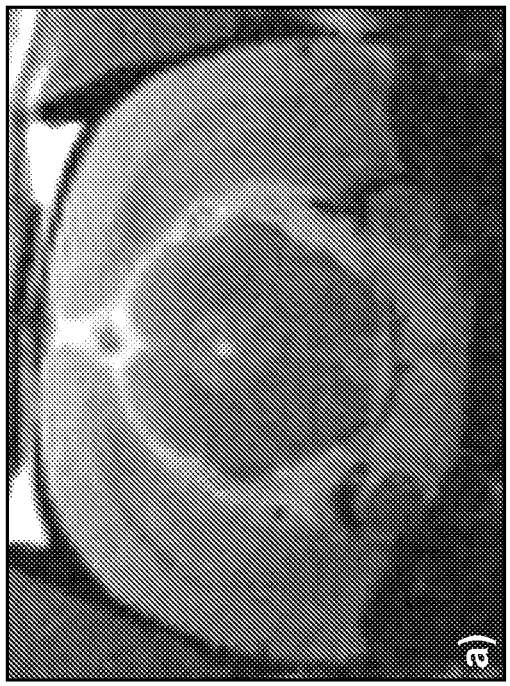
Figure 4:
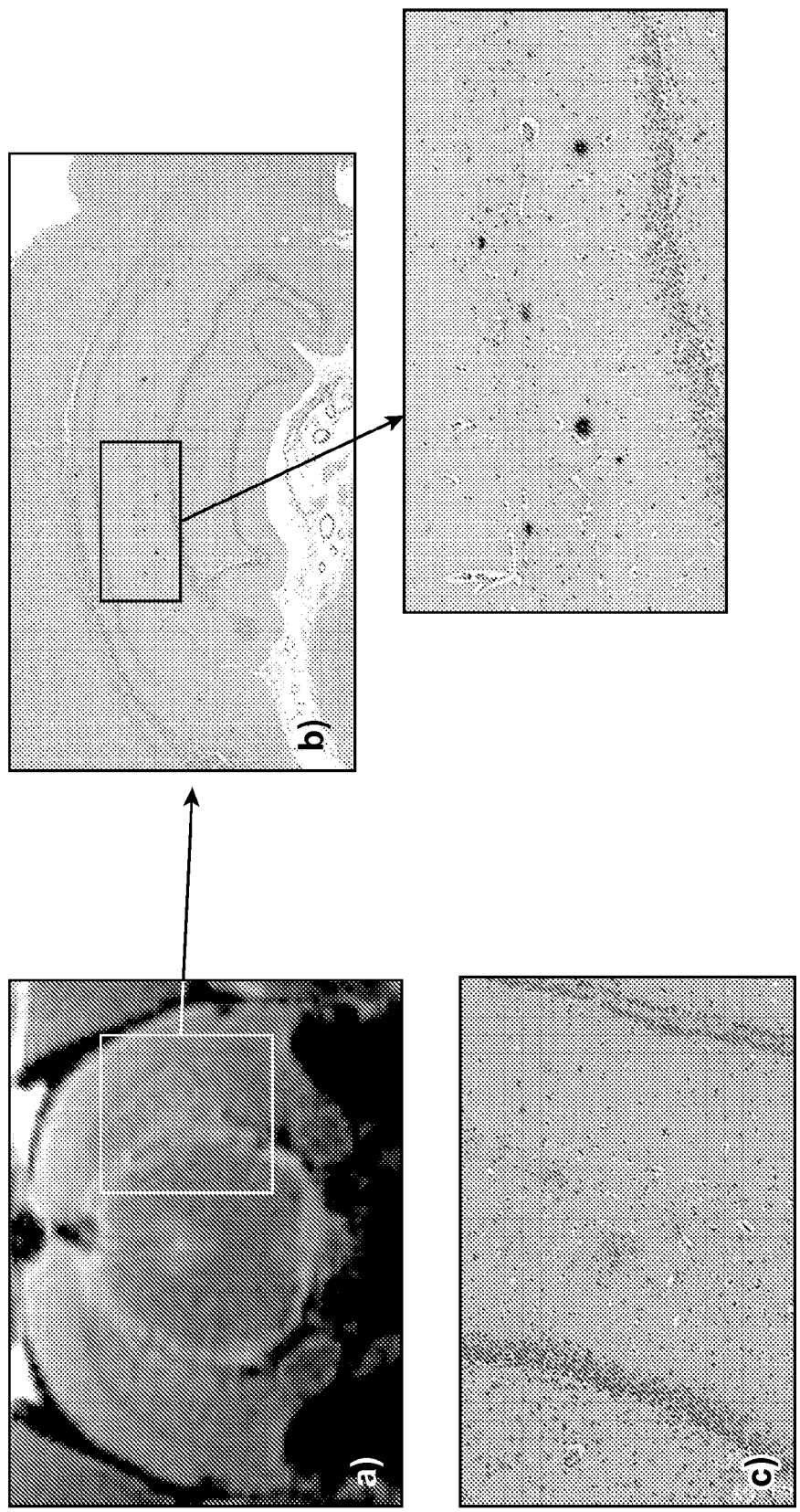
FIG. 4A-C depict representative MR images of the brain of a rat AD model.
Figure 5:
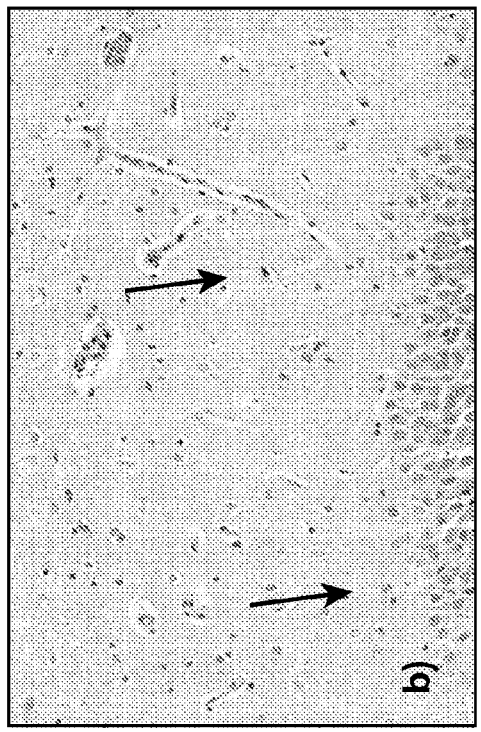
FIGS. 5A-D depict the presence of diffuse plaques in the brain of a rat AD model, using MRI. The rat AD model was administered DNP-MNP.
Figure 5:
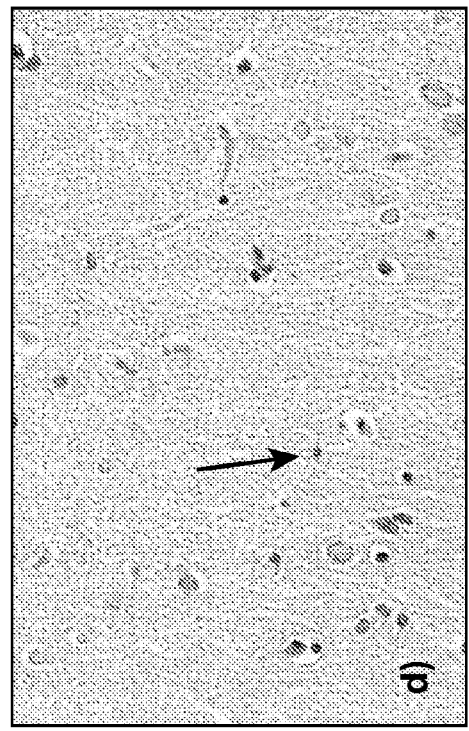
Figure 5:
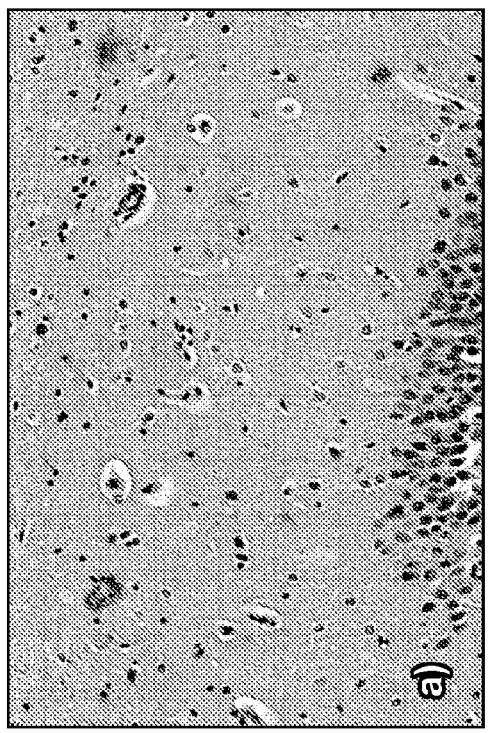
Figure 5:
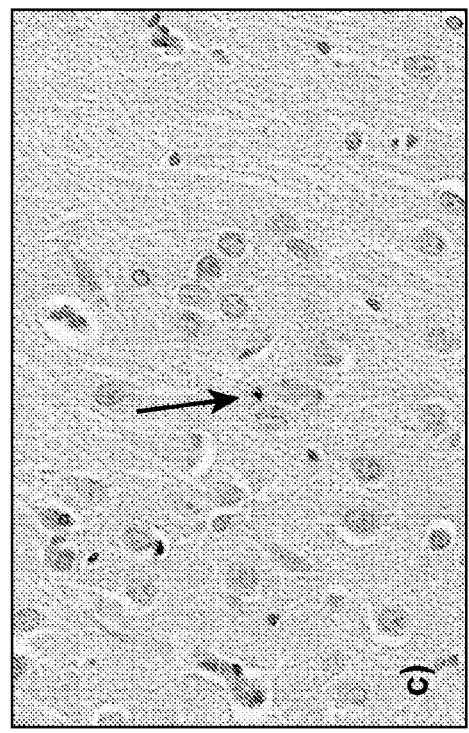
Figure 6:
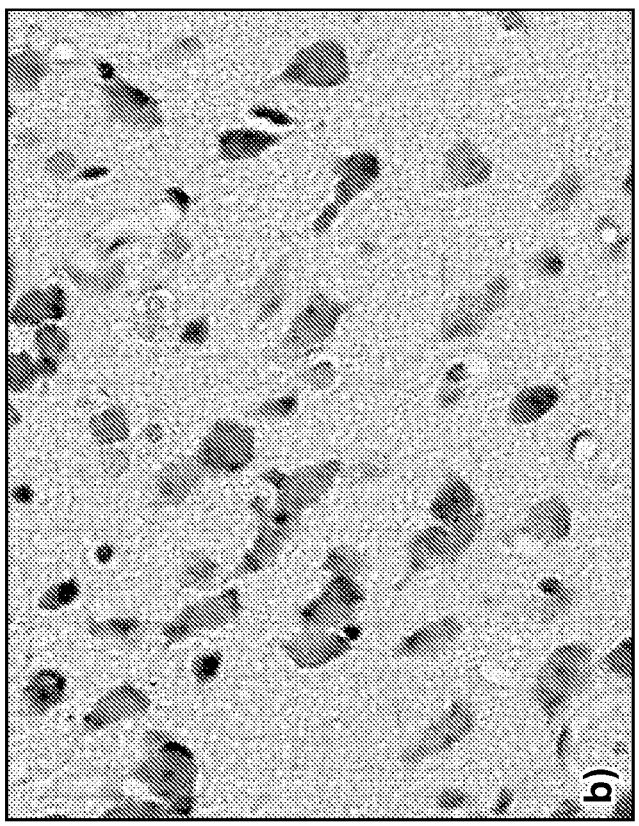
FIGS. 6A and 6B depict DAB-enhanced Perl's stain of a transgenic rat model of AD.
Figure 6:
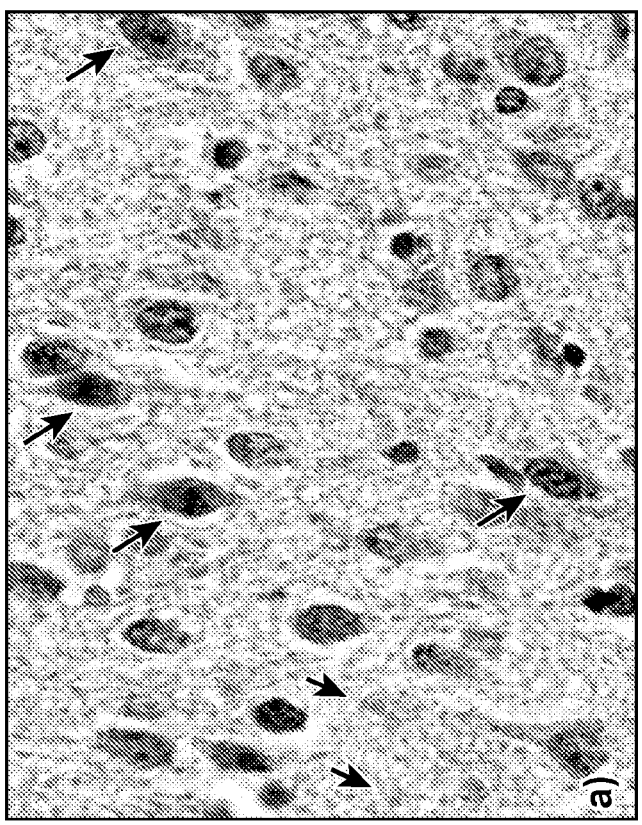

As used herein, the term "nanoparticle" refers to a particle having a diameter of between about 1 and 1000 nm. Similarly, by the term "nanoparticles" refers to a plurality of particles having an average diameter of between about 1 and 1000 nm.

Reference to the "size" of a nanoparticle is a reference to the length of the largest straight dimension of the nanoparticle. For example, the size of a perfectly spherical nanoparticle is its diameter.

As used herein, the term "functional group," used interchangeably with "functional moiety" and "functional ligand," refers to a chemical group that imparts a particular function to an article (e.g., nanoparticle) bearing the chemical group. For example, functional groups can include substances such as antibodies, oligonucleotides, biotin, or streptavidin that are known to bind particular molecules; or small chemical groups such as amines, carboxylates, and the like.

As used herein, "subject" or "individual" or "patient" refers to any subject for whom or which diagnosis, prognosis, or therapy is desired, and generally refers to the recipient of a diagnostic method, a prognostic method, or a therapeutic method, to be practiced according to the invention. The subject can be any mammal, e.g., a human, a non-human primate, a domestic livestock, a laboratory subject (e.g., a non-human animal model for a disease associated with β-amyloid deposits and/or NFT; e.g., a rodent such as a rat), or pet animal.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a functionalized magnetic nanoparticle" includes a plurality of such functionalized magnetic nanoparticles and reference to "the HODDNP moiety" includes reference to one or more HODDNP moieties and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides functionalized magnetic nanoparticles (MNPs) that are suitable for use in imaging brain tissue in a living individual who has or is suspected of having β-amyloid deposits and/or NFT. A subject functionalized MNP distinguishes between neurological tissue with amyloid deposits and/or neurofibrillary tangles (NFT, also known as paired helical filaments, PHF) and normal neurological tissue. A subject functionalized MNP can be used to detect and quantitate amyloid deposits and/or NFT in diseases including, for example, Down's syndrome or Alzheimer's Disease (AD).

A subject functionalized MNP can be used to detect and quantitate amyloid deposits and/or NFT in the brain of a living mammal, e.g., a human, a non-human animal, or a non-human animal model of a disease associated with or resulting from β-amyloid deposits and/or presence of NFT. A pharmaceutical composition comprising a subject functionalized MNP is administered to a living mammal. Any β-amyloid deposits (e.g., aggregated β-amyloid such as may be associated with neurofibrillary tangles) present in the brain can be visualized using magnetic resonance imaging (MRI) or any other appropriate imaging method.

Functional Moieties

Functional groups (moieties) that can be attached to a magnetic nanoparticle include functional groups that provide for binding to aggregates of β-amyloid peptides and/or NFT. Suitable functional groups that provide for binding to aggregates of β-amyloid peptides and/or NFT and that can be attached to a magnetic nanoparticle include 2-(1-{6-[(2-hydroxyethyl)(methyl)amino]-2-naphthyl}ethylidene)malononitrile (HODDNP), and analogs and derivatives thereof. Suitable functional groups that provide for binding to aggregates of β-amyloid peptides and that can be attached to a magnetic nanoparticle include (4'-aminophenyl)-6-hydroxybenzothiazole (PIB-2), and analogs and derivatives thereof.

HODDNP can be conjugated to an MNP through any of a number of attachment sites at the HODDNP molecule. HODDNP has the following formula:

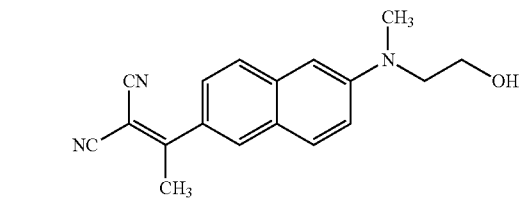 [SMILES: CC(=C(C#N)C#N)c1ccc2cc(N(C)CCO)ccc2c1]

For example, HODDNP can be conjugated to an MNP via the hydroxyl moiety of HODDNP. As one non-limiting example, HODDNP-conjugated MNPs can be prepared by covalently linking HODDNP to an epoxy-MNP via the hydroxyl moiety of HODDNP through an appropriate linker. HODDNP can be covalently or non-covalently bound to MNP directly or through an appropriate linker through any of the nitrogen or carbon moieties of the molecule or its modifications, precursors, derivatives, or variants.

PIB-2 can be conjugated to an MNP through any of a number of attachment sites at the PIB-2 molecule. PIB-2 has the following formula:

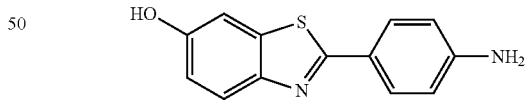

For example, PIB-2 can be conjugated to an MNP via the amino nitrogen of PIB-2. As one non-limiting example, PIB-2-conjugated MNPs can be prepared by covalently linking PIB-2 to an epoxy-MNP via the amino nitrogen of PIB-2 through an appropriate linker. Also, PIB-2 can be conjugated to an MNP via the phenolic oxygen of PIB-2. As one non-limiting example, PIB-2-conjugated MNPs can be prepared by covalently linking PIB-2 to an epoxy-MNP via the phenolic oxygen of PIB-2 through an appropriate linker.

PIB-2 can be covalently or non-covalently bound to MNP directly or through an appropriate linker through any of the nitrogen, oxygen, sulfur, or carbon moieties of the molecule or its modifications, precursors, derivatives, or variants.

Other suitable functional moieties that can be coupled to an MNP include, but are not limited to, 1) W-372 (7-Methoxy-2 (6-fluoropyridin-3-yl)imidazo[2,1-b]-8-pyridinothiazole)

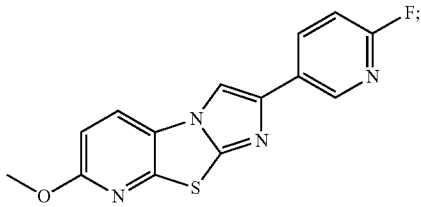 [SMILES: COc1ccc2c(n1)sc1nc(-c3ccc(F)nc3)cn12]

2) Bay-94-9172 (ZK 6013443; {4-[2-(4-{2-2[2-(2-Fluoro-ethoxy)-ethoxyl]-ethoxy}-phenyl)-vinyl]-phenyl}-methyl-amine))

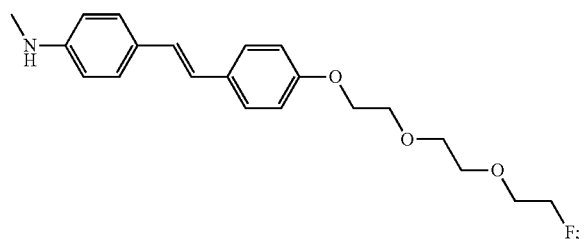

3) BF-227 (2-(2-[2-dimethylaminothiazol-5-yl]ethenyl)-6-(2-[fluoro]ethoxy)benzoxazole)

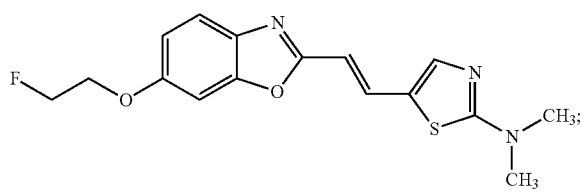 [SMILES: CN(C)c1ncc(/C=C/c2nc3ccc(OCCF)cc3o2)s1]

4) SB-13 (4-N-methylamino-4'-hydroxystilbene)

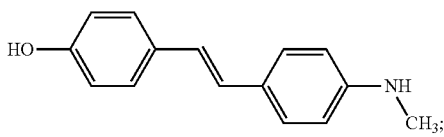

5) AV-45 ((E)-4-(2-(6-(2-(2-(2-(fluoroethoxy)ethoxy)ethoxy)pyridin-3-yl)vinyl)-N-methyl benzenamine)

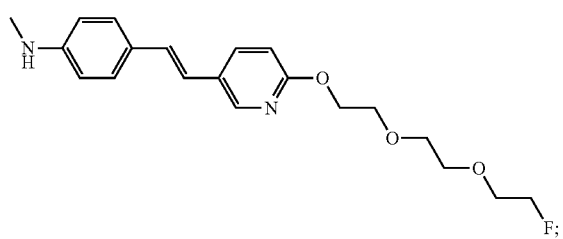 [SMILES: CNc1ccc(/C=C/c2ccc(OCCOCCOCCF)nc2)cc1]

6) AZD-2184 (2-[6-(methylamino)pyridin-3-yl]-1,3-benzothiazol-6-ol)

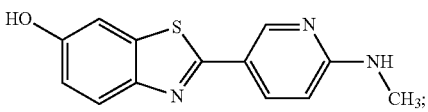

7) PK11195 (1-(2-chlorphenyl)-N-methyl-N-(1-methylpropyl)-3-isoquinoline-carboxamide)

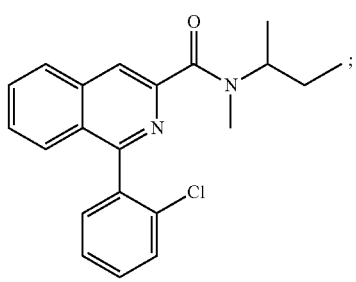 [SMILES: CCC(C)N(C)C(=O)c1cc2ccccc2c(-c2ccccc2Cl)n1]

8) DAA1106 (N-(2-phenoxy-5-fluorophenyl)-N-(2,5-dimethoxybenzyl)acetamide);

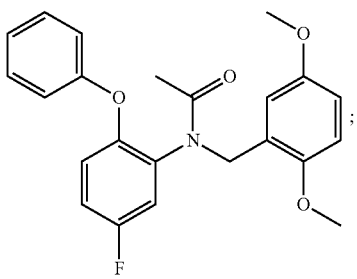 [SMILES: COc1ccc(OC)c(CN(C(C)=O)c2cc(F)ccc2Oc2ccccc2)c1]

and

9) DED (N,N-diethyldiethylenetriamine)

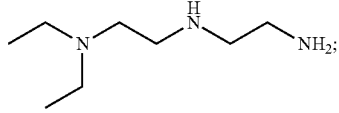

or a derivative or analog thereof.

In any of the foregoing functional moieties, a fluorine group can be replaced with oxygen. For example, the suitable functional moieties can be conjugated to an MNP via the hydroxyl moiety of the functional moiety. As one non-limiting example, functional moiety-conjugated MNPs can be prepared by covalently linking the functional moiety to an epoxy-MNP via the hydroxyl moiety of the functional moiety directly or through an appropriate linker. For example, other suitable functional moieties that can be coupled to an MNP include, but are not limited to,

1)

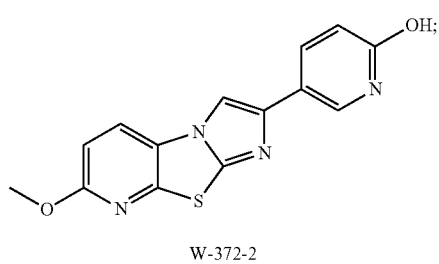

W-372-2

2)

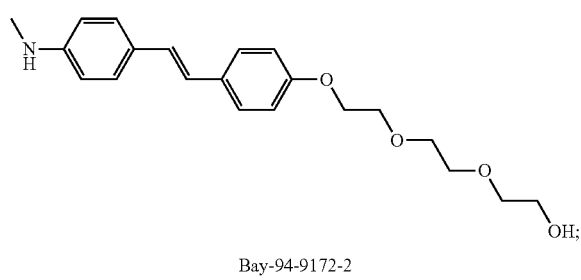

Bay-94-9172-2

3)

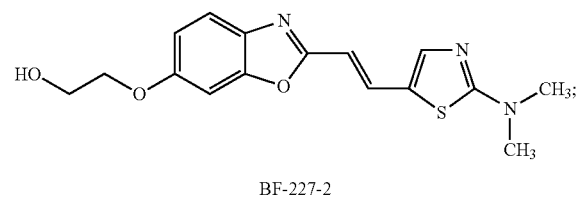

BF-227-2

4)

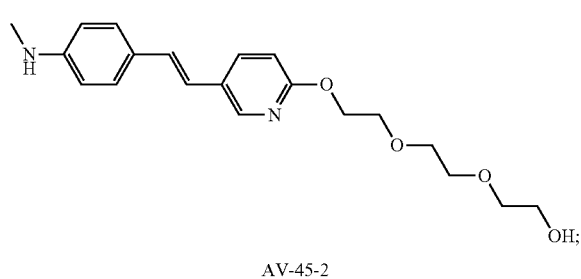

AV-45-2

5)

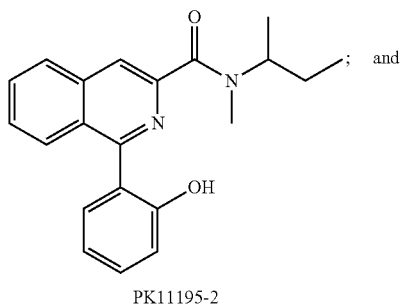

; and

PK11195-2

6)

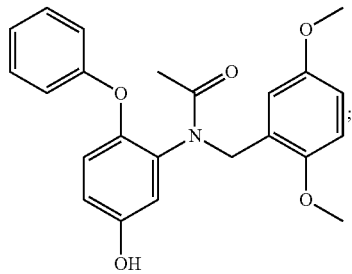

DAA1106-2 or a derivative or analog thereof.

In any of the foregoing functional moieties, a fluorine group can be replaced with an amino group. For example, a functional moiety comprising an amino group can be conjugated, directly or via a linker, to an MNP via the amino group of the functional moiety. As one non-limiting example, functional moiety-conjugated MNPs can be prepared by covalently linking the functional moiety to an epoxy-MNP via the amino group of the functional moiety through an appropriate linker. For example, other suitable functional moieties that can be coupled to an MNP include, but are not limited to,

1)

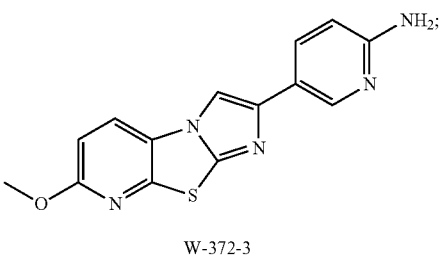

W-372-3

2)

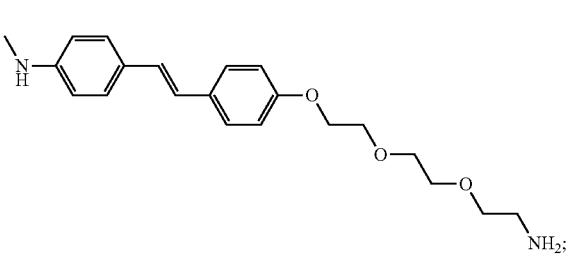

Bay-94-9172-3

3)

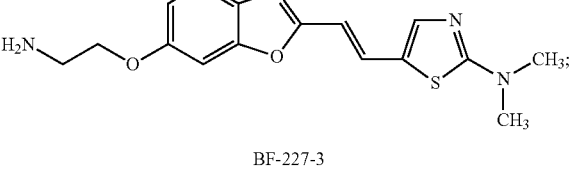

BF-227-3

4)

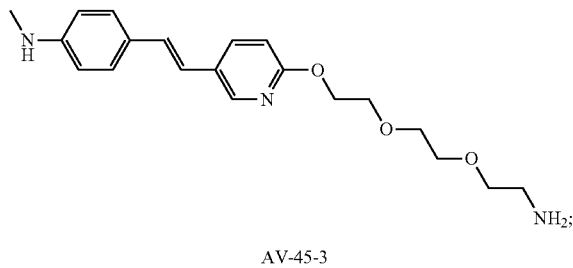

AV-45-3

5)

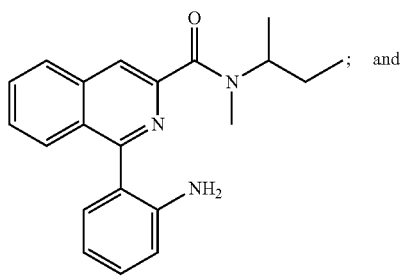

PK11195-3

6)

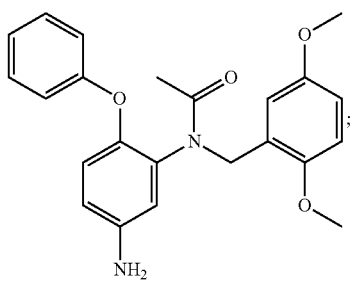

DAA1106-3 or a derivative or analog thereof.

In any of the foregoing functional moieties, a fluorine group can be replaced with a thiol group.

For example, a functional moiety comprising a thiol group can be conjugated, directly or via a linker, to an MNP via the thiol group of the functional moiety. As one non-limiting example, functional moiety-conjugated MNPs can be prepared by covalently linking the functional moiety to an epoxy-MNP via the thiol group of the functional moiety through an appropriate linker. For example, other suitable functional moieties that can be coupled to an MNP include, but are not limited to,

1)

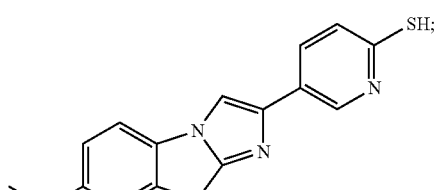

W-372-4

2)

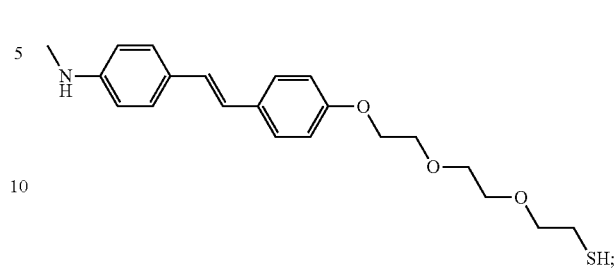

Bay-94-9172-4

3)

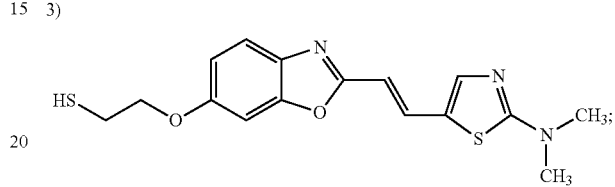

BF-227-4

4)

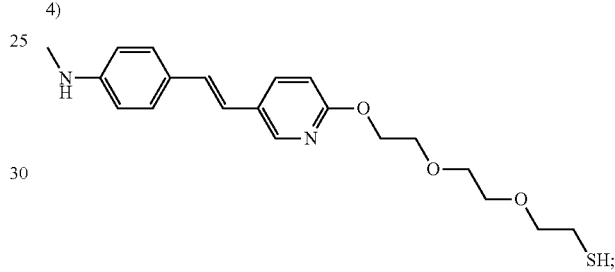

AV-45-4

5)

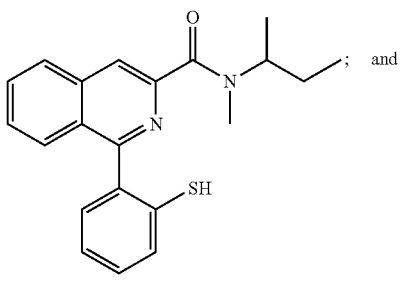

PK11195-4

6)

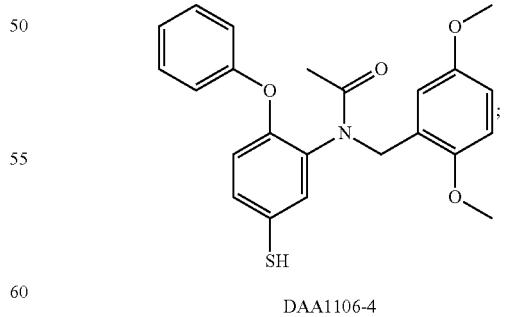

DAA1106-4 or a derivative or analog thereof.

In any of the foregoing functional moieties, an alkyl group can be replaced with hydroxyalkyl. For example, the suitable functional moieties can be conjugated, directly or via a linker, to an MNP via the hydroxyl moiety of the suitable functional moiety. As one non-limiting example, functional moiety-conjugated MNPs can be prepared by covalently linking the functional moiety to an epoxy-MNP via the hydroxyl moiety of the functional moiety through an appropriate linker. For example, other suitable functional moieties that can be coupled to an MNP include, but are not limited to, 1)
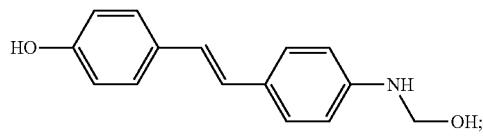
SB-13-5

2)
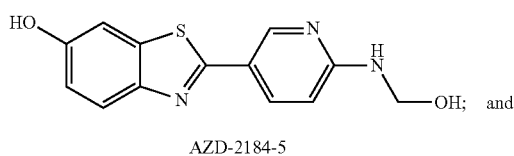
AZD-2184-5 and

3)
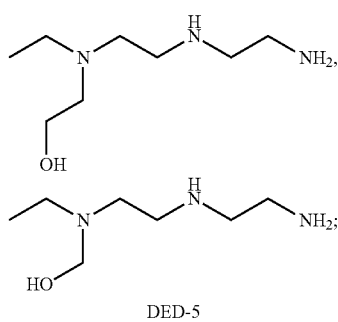
DED-5 or a derivative or analog thereof.

In any of the foregoing functional moieties, an alkyl group can be replaced with thioalkyl. For example, the suitable functional moieties can be conjugated to an MNP via the thiol moiety of the suitable functional moiety. As one non-limiting example, functional moiety-conjugated MNPs can be prepared by covalently linking the functional moiety to an epoxy-MNP via the thiol moiety of the functional moiety through an appropriate linker. For example, other suitable functional moieties that can be coupled to an MNP include, but are not limited to, 1) SB-13-6
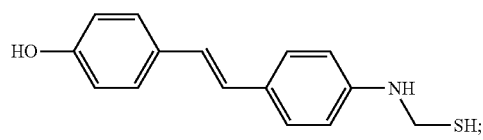

2) AZD-2184-6
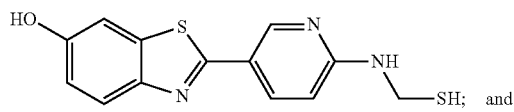
and

3) DED-6
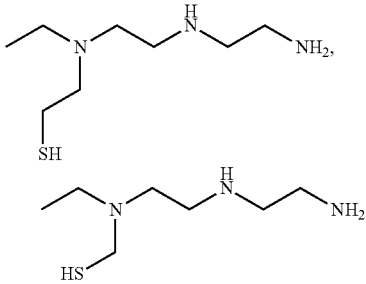

or a derivative or analog thereof.

A functional moiety of a subject functionalized MNP can have affinity for β-amyloid peptide (e.g., aggregated β-amyloid peptide) and/or NFT. For example, the functional moiety can have an affinity of from about $10^{-6}$ M, $10^{-7}$ M, $10^{-8}$ M, or greater than $10^{-8}$ M, for β-amyloid peptide (e.g., aggregated β-amyloid peptide) and/or NFT.

A subject functionalized MNP may include a radiolabel, e.g., the functional moiety can include a radiolabel. Alternatively, a subject functionalized MNP does not include a radiolabel, e.g., the functional moiety does not include a radiolabel, and no other component of the functionalized MNP comprises a radiolabel.

A subject functionalized MNP can cross the blood-brain barrier. A subject functionalized MNP provides contrast in T2, T2*, and T1 times of affected tissues (e.g., brain tissues with β-amyloid deposits and/or NFT) to render the tissues visible to MRI.

A subject functionalized MNP has a relatively long half-life (e.g., a $t_{1/2}$ of from about 2 hours to about 14 days; e.g., from about 2 hours to about 4 hours, from about 4 hours to about 8 hours, from about 8 hours to about 16 hours, from about 16 hours to about 24 hours, from about 24 hours to about 2 days, from about 2 days to about 4 days, from about 4 days to about 7 days, or from about 7 days to about 2 weeks).

Magnetic Nanoparticles

Subject nanoparticles generally have a mean size in a range of from about 1 nm to about 1000 nm, e.g., from about 1 nm to about 10 nm, from about 10 nm to about 50 nm, from about 50 nm to about 100 nm, from about 100 nm to about 250 nm, from about 250 nm to about 500 nm, from about 500 nm to about 750 nm, or from about 750 nm to about 1000 nm. Average diameters will in some embodiments range from about 10 nm to about 1000 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, or from about 800 nm to about 1000 nm.

Nanoparticles can be simple aggregations of molecules or they can be structured into two or more layers of different substances. For example, simple nanoparticles consisting of magnetite or maghemite are suitable for use. See, e.g., Scientific and Clinical Applications of Magnetic Microspheres, U. Hafeli, W. Schutt, J. Teller, and M. Zborowski (eds.) Plenum Press, New York, 1997; and Tiefenauer et al., Bioconjugate Chem. 4:347, 1993. More complex nanoparticles can consist of a core made of one substance and one or more shells made of another substance(s). The term "magnetic nanoparticle" includes paramagnetic nanoparticles, diamagnetic nanoparticles, and ferromagnetic nanoparticles.

Exemplary core materials of the nanoparticles according to the invention are ferrites of general composition $MeOxFe_2O_3$ wherein Me is a bivalent metal such as Co, Mn or Fe. Other suitable materials are $\gamma$-$Fe_2O_3$, the pure metals Co, Fe, Ni, and metal compounds such as carbides and nitrides. The core material is generally an MRI visible agent. The core material is typically coated. Suitable coatings include, but are not limited to, dextran, albumin, starch, silicon, and the like.

Many different type of small particles (nanoparticles or micron-sized particles) are commercially available from several different manufacturers including: Bangs Laboratories (Fishers, Ind.); Promega (Madison, Wis.); Dynal Inc. (Lake Success, N.Y.); Advanced Magnetics Inc. (Surrey, U.K.); CPG Inc. (Lincoln Park, N.J.); Cortex Biochem (San Leandro, Calif.); European Institute of Science (Lund, Sweden); Ferrofluidics Corp. (Nashua, N.H.); FeRx Inc.; (San Diego, Calif.); Immunicon Corp.; (Huntingdon Valley, Pa.); Magnetically Delivered Therapeutics Inc. (San Diego, Calif.); Miltenyi Biotec GmbH (USA); Microcaps GmbH (Rostock, Germany); PolyMicrospheres Inc. (Indianapolis, Ind.); Scigen Ltd. (Kent, U.K.); Seradyn Inc.; (Indianapolis, Ind.); and Spherotech Inc. (Libertyville, Ill.). Most of these particles are made using conventional techniques, such as grinding and milling, emulsion polymerization, block copolymerization, and microemulsion.

Methods of making silica nanoparticles have also been reported. The processes involve crystallite core aggregation (Philipse et al., Langmuir, 10:92, 1994); fortification of superparamagnetic polymer nanoparticles with intercalated silica (Gruttner, C and J Teller, Journal of Magnetism and Magnetic Materials, 194:8, 1999); and microwave-mediated self-assembly (Correa-Duarte et al., Langmuir, 14:6430, 1998).

Subject nanoparticle cores are magnetic and can include a metal selected from the group consisting of magnetite, maghemite, and greigite. Magnetic nanoparticles can be made using magnetic materials such as magnetite, maghemite, and greigite as part of the core. By varying the overall size and shape of such magnetic cores, they can be made superparamagnetic or stable single-domain (particles that retain a stable magnetic moment after being removed from a magnetic field). Core size relates to whether a magnetic nanoparticle is superparamagnetic or single-domain. Thus, relatively equidimensional superparamagnetic particles generally have a core sized less than 50 to 80 nm. At particle sizes above this upper range, the magnetization of the particle is split into domains of differing magnetization vectors in order to minimize internal magnetic energies.

In some embodiments, the core includes a pigment which can be an inorganic salt such as potassium permanganate, potassium dichromate, nickel sulfate, cobalt chloride, iron (III) chloride, or copper nitrate. Similarly, the core can include a dye such as Ru/Bpy, Eu/Bpy, or the like; or a metal such as Ag and Cd.

In some embodiments, a subject modified nanoparticle comprises a core and a silica shell enveloping the core. The functional group is conjugated to the silica shell, e.g., as described in U.S. Pat. No. 6,548,264. Numerous known methods for attaching functional groups to silica can be adapted for use in the present invention. See, e.g., Ralph K. Iler, The Chemistry of Silica: Solubility, Polymerization, Colloid and Surface Properties, and Biochemistry, Wiley-Interscience, NY, 1979; VanDerVoort, P. and Vansant, E. F., Journal of Liquid Chromatography and Related Technologies, 19:2723-2752, 1996; and Immobilized Enzymes. Antigens, Antibodies, and Peptides: Preparation and Characterization, Howard H. Weetall (ed.), M. Dekker, NY, 1975. A typical process for adding functional groups to silica-coated nanoparticles involves treating the nanoparticles with a silanizing agent that reacts with and couples a chemical group to the silica surface of the nanoparticles. The chemical group can itself be the functional group, or it can serve as a substrate to which functional groups can be coupled.

For example, in an exemplary method, silica-coated nanoparticles are prepared as described above and the particle surfaces are silanized using trimethylsilylpropyl-diethylenetriamine (DETA), a silanization agent that attaches primary amine groups to silica surfaces. A functional group can then be covalently coupled to the silanized surface using the cyanogen bromide (CNBR) method. As one example, CNBR-mediated coupling can be achieved by suspending silica-coated nanoparticles previously silanized with DETA in a 2 M sodium carbonate buffer and ultrasonicating the mixture to create a particle suspension. A solution of CNBR (e.g., 2 g CNBR/1 ml acetonitirile) is then added to the particle suspension to activate the nanoparticles. After washing the nanoparticles with a neutral buffer (e.g., PBS, pH 8), an antibody solution is added to the activated nanoparticle suspension causing the antibodies to become bound to the nanoparticles. A glycine solution can also be added to the antibody-coated nanoparticles to block any remaining unreacted sites.

In some embodiments, the magnetic nanoparticle is dextran coated. Magnetic nanoparticles are made using any known process. For example, magnetic iron-dextran particles are prepared by mixing 10 ml of 50% (w/w) aqueous Dextran T-40 (Pharmacia) with an equal volume of an aqueous solution containing 1.51 g $FeCl_3$-$6H_2O$ and 0.64 g $FeCl_2$-$4H_2O$. While stirring, the mixture is titrated to pH 10-11 by the drop-wise addition of 7.5% (v/v) $NH_4OH$ heated to 60-65° C. in a water bath for 15 minutes. Aggregates are then removed by 3 cycles of centrifugation in a low-speed clinical centrifuge at 600×g for 5 minutes. The ferromagnetic iron-dextran particles are separated from unbound dextran by gel filtration chromatography on Sephacryl-300. Five ml of the reaction mixture is then applied to a 2.5×33 cm column and eluted with 0.1 M sodium acetate and 0.15 M NaCl at pH 6.5. The purified ferromagnetic iron-dextran particles collected in the void volume will have a concentration of 7-10 mg/ml as determined by dry weight analysis. Molday and Mackenzie (1982) Journal of Immunological Methods 52:353-367. Also see (Xianqiao (2003) China Particuology Vol. 1, No. 2, 76-79). The resulting magnetonanoparticles can be separated based on size and or magnetic properties through high-gradient magnetic field separation with appropriate magnetic field strength.

Figure 8:
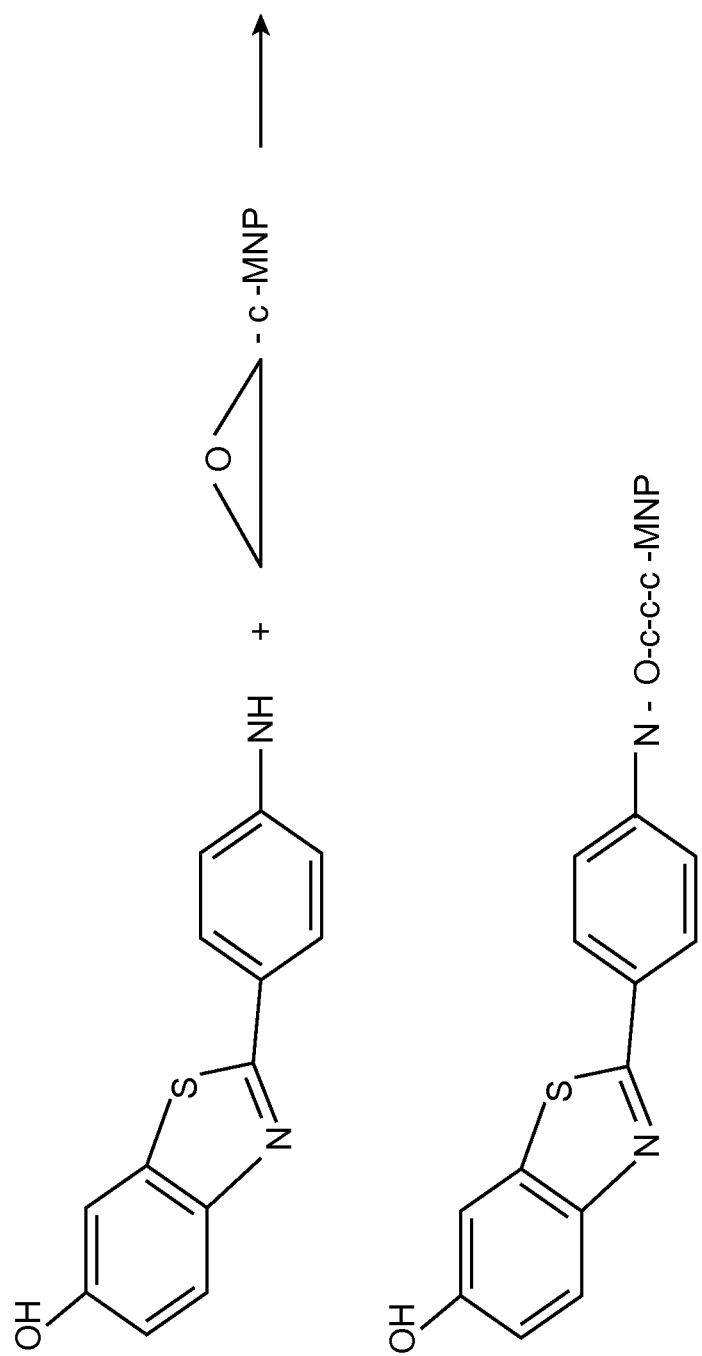
FIG. 8 depicts a method of conjugating (4'-aminophenyl)-6-hydroxybenzothiazole (PIB-2) to a magnetic nanoparticle.

In some embodiments, the coated nanoparticles can comprise an epoxide group. FIGS. 8 and 9 illustrate examples of coated nanoparticles comprising an epoxide group. For a silica-coated nanoparticle, the silica coating can comprise an epoxide group. For example, an epoxysilane can be used. For a dextran-coated nanoparticle, the dextran coating can comprise an epoxide group. For example, an epoxy-modified dextran can be produced by reaction of dextran with reagents that have epoxide groups. For example, the hydroxyl groups of dextran can react to form silylated dextran comprising epoxide groups.

The coating can have a thickness (e.g., the average distance from the outside surface of the core magnetic particle to the outside surface of the coating) of from about 1 nm to about 500 nm, e.g., from about 1 nm to about 5 nm, from about 5 nm to about 10 nm, from about 10 nm to about 15 nm, from about 15 nm to about 20 nm, from about 20 nm to about 25 nm, from about 25 nm to about 30 nm, from about 30 nm to about 40 nm, from about 40 nm to about 50 nm, from about 50 nm to about 60 nm, from about 60 nm to about 70 nm, from about 70 nm to about 80 nm, from about 80 nm to about 90 nm, from about 90 nm to about 100 nm, from about 100 nm to about 125 nm, from about 125 nm to about 150 nm, from about 150 nm to about 175 nm, from about 175 nm to about 200 nm, from about 200 nm to about 225 nm, from about 225 nm to about 250 nm, from about 250 nm to about 275 nm, from about 275 nm to about 300 nm.

The ratio of the thickness of the coating to the diameter of the magnetic core particle is from about 1:1 to about 1:1000, e.g., from about 1:1 to about 1:1.5, from about 1:1.5 to about 1:2, from about 1:2 to about 1:2.5, from about 1:2.5 to about 1:5, from about 1:5 to about 1:10, from about 1:10 to about 1:25, from about 1:25 to about 1:50, from about 1:50 to about 1:100, from about 1:100 to about 1:250, from about 1:250 to about 1:500, from about 1:500 to about 1:750, or from about 1:750 to about 1:1000.

In some embodiments, a subject functionalized magnetic nanoparticle is of the formula: M-(L)-Z, the linkage sites between L and Z having covalently bound functional groups, wherein M represents the magnetic core particle, L represents an optional linker group, and Z represents a functional group. In other embodiments, a subject functionalized magnetic nanoparticle is of the formula: M-S-(L)-Z, the linkage sites between S and L and L and Z having covalently bound functional groups, wherein M represents the magnetic core particle, wherein S represents a biocompatible substrate fixed to M, wherein M represents the magnetic core particle, L represents an optional linker group, and Z represents a functional group. Functional groups include moieties that provide for binding to β-amyloid peptides (e.g., aggregated β-amyloid peptide) and/or NFT; moieties that provide for crossing the BBB; therapeutic agents; and the like.

In some embodiments, a subject functionalized magnetic nanoparticle comprises two or more different functional groups attached to the same core particle. For example, in some embodiments, a subject functionalized magnetic nanoparticle is of the formula M-(L)-$Z_1Z_2$, or M-S-(L)-$Z_1Z_2$, where $Z_1$ and $Z_2$ are different functional groups. In some embodiments, for example, $Z_1$ is a binding moiety β-amyloid peptides (e.g., aggregated β-amyloid peptide) and/or NFT; and $Z_2$ is a therapeutic agent. In other embodiments, for example, $Z_1$ is a moiety that provides for crossing the BBB; and $Z_2$ is a binding moiety that provides for binding to β-amyloid peptides (e.g., aggregated β-amyloid peptide) and/or NFT. The $Z_1$ and $Z_2$ moieties are independently attached to the core particle or the polymer, directly or via a linker. In some embodiments, a subject functionalized magnetic nanoparticle comprises at least a third functional moiety $Z_3$.

The magnetic core particles consist of magnetite, maghemite, ferrites of general formula MeOxFe2O3 wherein Me is a bivalent metal such as cobalt, manganese, iron, or of cobalt, iron, nickel, iron carbide, or iron nitride, as described above. If present, the substrate S is formed by compounds such as polysaccharides or oligosaccharides or derivatives thereof, such as dextran, carboxymethyldextran, starch, dialdehyde starch, chitin, alginate, cellulose, carboxymethylcellulose, proteins or derivatives thereof, such as albumins, peptides, synthetic polymers, such as polyethyleneglycols, polyvinylpyrrolidone, polyethyleneimine, polymethacrylates, bifunctional carboxylic acids and derivatives thereof, such as mercaptosuccinic acid or hydroxycarboxylic acids.

The linker group L is formed by reaction of a compound such as poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups.

A subject functionalized magnetic nanoparticle is capable of passing the blood-brain barrier. For example, a subject functionalized magnetic nanoparticle may comprise, attached to the nanoparticle, or in a formulation with the nanoparticle, or coating the nanoparticle, one or more polymers. Suitable polymers that facilitate crossing of the blood brain barrier include, but are not limited to, surfactants such as polysorbate (e.g., Tween® 20, 40, 60 and 80); poloxamers such as Pluronic® F 68; and the like. In some embodiments, a subject functionalized magnetic nanoparticle is coated with a polysorbate such as, e.g., Tween® 80 (which is Polyoxyethylene-80-sorbitan monooleate), Tween® 40 (which is Polyoxyethylene sorbitan monopalmitate); Tween® 60 (which is Polyoxyethylene sorbitan monostearate); Tween® 20 (which is Polyoxyethylene-20-sorbitan monolaurate); polyoxyethylene 20 sorbitan monopalmitate; polyoxyethylene 20 sorbitan monostearate; polyoxyethylene 20 sorbitan monooleate; etc. Also suitable for use are water soluble polymers, including, e.g.: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); dextran, and proteins such as albumin. Block co-polymers are suitable for use, e.g., a polyethylene oxide-polypropylene oxide-polyethylene-oxide (PEO-PPO-PEO) triblock co-polymer (e.g., Pluronic® F68); and the like; see, e.g., U.S. Pat. No. 6,923,986. Other methods for crossing the blood brain barrier are discussed in various publications, including, e.g., Chen et al. (2004) Curr. Drug Delivery 1:361-376.

In some embodiments, a subject functionalized MNP comprises one or more agents that provide for evasion of the reticuloendothelial system (RES). Agents that provide for evasion of the RES include, but are not limited to, a block copolymer non-ionic surfactant such as a poloxamine, such as poloxamine 508, poloxamine 908, poloxamine 1508, etc. In some embodiments, a subject functionalized MNP comprises about 1% poloxamine.

Nanoparticles can also be transferred across the blood-brain barrier (BBB) by utilizing the specific delivery channels that are present in the BBB. As one non-limiting example, attachment of 2-deoxy glucose to the nanoparticles renders the glucose channels receptive to these particles and aids in delivery across the BBB. Other mechanisms are transcytosis and diapedesis, with or without the mediation of the channels present at the BBB.

A subject functionalized magnetic nanoparticle can be delivered to the central nervous system (CNS) using a neurosurgical techniques. In the case of gravely ill patients such as accident victims or those suffering from various forms of dementia, surgical intervention is warranted despite its attendant risks. For instance, a subject functionalized magnetic nanoparticle can be delivered by direct physical introduction into the CNS, such as intraventricular or intrathecal injection. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) Fed. Proc. 43:214-219; Baba et al. (1991) J. Cereb. Blood Flow Metab. 11:638-643; and Gennuso et al. (1993) Cancer Invest. 11:638-643.

Further, it may be desirable to administer a subject functionalized magnetic nanoparticle locally to the area in need of diagnosis or treatment; this may be achieved by, for example, local infusion during surgery, by injection, by means of a catheter, or by means of an implant, said implant being of a porous, non-porous, or gelatinous material, including membranes, such as silastic membranes, or fibers.

A subject functionalized magnetic nanoparticle can also be delivered by using pharmacological techniques including chemical modification such that the subject functionalized magnetic nanoparticle will cross the blood-brain barrier. The subject functionalized magnetic nanoparticle may be modified to increase the hydrophobicity of the nanoparticle, decrease net charge or molecular weight of the nanoparticle, or modify the nanoparticle, so that it will resemble one normally transported across the blood-brain barrier. Levin (1980) J. Med. Chem. 23:682-684; Pardridge (1991) in: Peptide Drug Delivery to the Brain; and Kostis et al. (1994) J. Clin. Pharmacol. 34:989-996.

Encapsulation of the subject functionalized magnetic nanoparticle in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating a subject functionalized magnetic nanoparticle to pass through the blood-brain barrier is to encapsulate the subject functionalized magnetic nanoparticle in a cyclodextrin. Any suitable cyclodextrin which passes through the blood-brain barrier may be employed, including, but not limited to, α-cyclodextrin, β-cyclodextrin and derivatives thereof. See generally, U.S. Pat. Nos. 5,017,566, 5,002,935 and 4,983,586. Such compositions may also include a glycerol derivative as discussed in U.S. Pat. No. 5,153,179.

In some embodiments, a subject functionalized magnetic nanoparticle is capable of entering a cell in the brain, e.g., crossing a cell membrane and entering the cytoplasm of the cell. Mechanisms for entering a cell in the brain include, e.g., transcytosis and diapedesis, with or without mediation of appropriate membrane channels.

Therapeutic Agents

A subject functionalized MNP can include, in addition to a functional group that binds β-amyloid deposits and or NFT, a therapeutic agent, e.g., a therapeutic agent suitable for treating AD. Suitable therapeutic agents include agents for treating AD, where such agents include, but are not limited to, acetylcholinesterase inhibitors, including, but not limited to, Aricept (donepezil), Exelon (rivastigmine), metrifonate, Razadyne (galantamine), and tacrine (Cognex); non-steroidal anti-inflammatory agents, including, but not limited to, ibuprofen and indomethacin; cyclooxygenase-2 (Cox2) inhibitors such as Celebrex; monoamine oxidase inhibitors, such as Selegilene (Eldepryl or Deprenyl); and N-methyl D-aspartate (NMDA) antagonists such as Namenda (memantine).

Another suitable additional therapeutic agent for treating AD is an apoE4 "structure corrector" that reduces apoE4 domain interaction. Agents that reduce apoE4 domain interaction include, e.g., an agent as described in U.S. Patent Publication No. 2006/0073104); and in Ye et al. (2005) Proc. Natl. Acad. Sci. USA 102:18700.

Another suitable additional therapeutic agent for treating AD is an agent that inhibits tau aggregation, e.g., a napthoquinone derivative that inhibits tau aggregation, as described in U.S. Pat. No. 7,605,179. Another suitable additional therapeutic agent is an agent that inhibits phosphorylation of tau, e.g., a 3-substituted-4-pyrimidone derivative that inhibits tau protein kinase 1, as described in U.S. Pat. No. 7,572,793.

Compositions

The present disclosure further provides compositions, including pharmaceutical compositions, comprising a subject functionalized MNP. Compositions comprising a subject functionalized magnetic nanoparticle will include one or more of the following: a salt; a buffer; a pH adjusting agent; a non-ionic detergent; a protease inhibitor; a nuclease inhibitor; and the like.

A pharmaceutical composition comprising a subject functionalized MNP will comprise one or more pharmaceutically acceptable carriers. As used herein, "pharmaceutically acceptable carrier" includes any material which, when combined with an active ingredient of a composition, allows the ingredient to retain biological activity and without causing disruptive reactions with the subject's immune system or other physiological function. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well-known conventional methods (see, for example, Remington's Pharmaceutical Sciences, Chapter 43, 14th Ed., Mack Publishing Col, Easton Pa. 18042, USA). Pharmaceutically acceptable excipients have been amply described in a variety of publications, including, for example, A. Gennaro (2000) "Remington: The Science and Practice of Pharmacy," 20th edition, Lippincott, Williams, & Wilkins; Remington's Pharmaceutical Sciences, 14th Ed. or latest edition, Mack Publishing Col, Easton Pa. 18042, USA; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A subject functionalized magnetic nanoparticle can be formulated into preparations for injection by dissolving, suspending or emulsifying in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Imaging Methods

A subject functionalized MNP can be used to detect and quantitate amyloid deposits and/or NFT in the brain of a living mammal, e.g., a human, a non-human animal, or a non-human animal model of a disease associated with or resulting from β-amyloid deposits and/or NFT. A pharmaceutical composition comprising a subject functionalized MNP is administered to a living mammal. Any β-amyloid deposits (e.g., aggregated β-amyloid such as may be associated with neurofibrillary tangles) present in the brain can be visualized using magnetic resonance imaging (MRI) or any other appropriate imaging method. Thus, the present disclosure provides methods of detecting and quantitating amyloid deposits and/or NFT in the brain of a living mammal. The methods generally involve administering to a mammal a diagnostically effective amount of a pharmaceutical composition comprising a subject functionalized MNP; and b) imaging the brain tissue via MRI. The administered functionalized MNP is allowed to distribute into the brain tissue, and any functionalized MNP bound to aggregated β-amyloid peptides and/or NFT can be imaged using MRI. An increase in binding of the functionalized MNP to the brain tissue compared to a normal control level of binding indicates that the mammal is suffering from or is at risk of developing Alzheimer's Disease.

A subject functionalized MNP provides contrast in T2, T2*, and T1 times of affected tissues (e.g., brain tissues with β-amyloid deposits) to render the tissues visible to MRI. Regions of interest to be imaged include, e.g., the hippocampus, the cortex, and the midbrain.

A subject functionalized MNP can be used to image β-amyloid deposits (e.g., aggregated β-amyloid protein) and/or NFT in the brain of a non-human animal model of Alzheimer's disease (AD), e.g., for research purposes. Suitable non-human animal models of AD include a transgenic mouse comprising a human amyloid precursor protein (hAPP) mutant transgene; a transgenic mouse comprising a presenilin1 or a presenilin2 transgene; and the like. See, e.g., Götz et al. (2004) *Mol. Psychiatry.* 9:664; Götz and Ittner (2008) *Nature Reviews* 9:532.

For example, an experimental drug for the treatment of AD can be administered to a non-human animal model of AD; and a subject functionalized MNP can be used to determine the effect of the experimental drug on the amount of β-amyloid deposits and/or NFT in the brain of the non-human animal model.

In carrying out a subject imaging method, a subject functionalized MNP can be administered to an individual by any of a variety of routes of administration, including parenteral and enteral routes. Suitable routes of administration include, e.g., intravenous, oral, rectal, vaginal, nasal, ocular, intrathecal, intracranial, intramuscular, etc.

Treatment Methods

As noted above, in some embodiments, a subject functionalized MNP can include, in addition to a functional moiety (group) that binds β-amyloid deposits and/or NFT, a therapeutic agent. Such a functionalized MNP can be used in imaging and/or treatment of AD.

Suitable therapeutic agents include agents for treating AD, where such agents include, but are not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl).

Another suitable additional therapeutic agent for treating AD is an apoE4 "structure corrector" that reduces apoE4 domain interaction. Agents that reduce apoE4 domain interaction include, e.g., an agent as described in U.S. Patent Publication No. 2006/0073104); and in Ye et al. (2005) Proc. Natl. Acad. Sci. USA 102:18700.

Another suitable additional therapeutic agent for treating AD is an agent that inhibits tau aggregation, e.g., a napthoquinone derivative that inhibits tau aggregation, as described in U.S. Pat. No. 7,605,179. Another suitable additional therapeutic agent is an agent that inhibits phosphorylation of tau, e.g., a 3-substituted-4-pyrimidone derivative that inhibits tau protein kinase 1, as described in U.S. Pat. No. 7,572,793.

In carrying out a subject treatment method, a subject functionalized MNP can be administered by any of a variety of routes of administration, including parenteral and enteral routes. Suitable routes of administration include, e.g., intravenous, oral, rectal, vaginal, nasal, ocular, intrathecal, intracranial, intramuscular, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Preparation of Functionalized MNPs

HODDNP-conjugated MNPs ("DNP-MNPs")

HODDNP-conjugated MNPs were administered to naïve (no AD) rats and to a rat model of AD. The data are shown in FIGS. 1-6.

FIGS. 1A and 1B. MR (magnetic resonance) images (T2, TR 6000 milliseconds (ms), TE 10-120 ms, 12 echoes) of a naïve (non-AD) rat are shown. FIG. 1A shows the baseline (pre-contrast) MR image of a representative slice. FIG. 1*b* shows the post-contrast MR image of the same slice. Comparison of quantitative T2 values of the volumetric regions of interest (ROI) (where the ROIs include hippocampus, cortex, midbrain) in the baseline (FIG. 1A) and post-contrast (FIG. 1B) scans did not show significant ($p>0.05$) contrast enhancement in this naïve animal following injection with DNP-MNP (also referred to as "HODDNP-MNP").

Table 1 shows the quantitative T2 values ("Base T2 (ms)") of the regions of interest (ROIs) (where the ROIs include hippocampus, cortex, midbrain) in the baseline scan. Table 1 shows the quantitative T2 values ("Post T2") of the same regions of interest in the same rat 1.5 hours after intravenous (i.v.; tail vein) injection of HODDNP-MNP.

TABLE 1

| ROI | Base T2 (ms) | Post T2 |
| --- | --- | --- |
| Hippocampus | 55.0 ± 0.2 | 51.3 ± 0.3 |
| cortex | 53.0 ± 0.3 | 48.6 ± 0.2 |
| midbrain | 50.7 ± 0.4 | 46.5 ± 0.4 |

FIGS. 2A and 2B. MR images (T2, TR 6000 ms, TE 10-120 ms, 12 echoes) of a 1-year-old rat that is a genetic model of AD (triple genetic model of amyloid-β (Aβ) plaques) are shown. FIG. 2A shows the baseline (pre-contrast) MR image of a representative slice in this rat. FIG. 2B shows the post-contrast MR image of the same slice, 2.5 hours after injection with contrast. Comparison of quantitative T2 values of the volumetric ROIs (hippocampus, cortex, and midbrain) in the baseline (FIG. 2A) and post-contrast (FIG. 2B) scans showed significant (P<0.05) contrast enhancement in all ROIs following injection with DNP-MNP. Contrast enhancement was most prominent in the hippocampus, followed by the cortex.

Table 2 shows the quantitative T2 values ("Base T2 (ms)") of the ROIs (hippocampus, cortex, and midbrain) in the baseline scan. Table 2 shows the quantitative T2 values ("Post T2") of the same ROIs in the same rat 2.5 hours after i.v. (tail vein) injection of HODDNP-MNPs.

TABLE 2

| ROI | Base T2 (ms) | Post T2 |
|---|---|---|
| hippocampus | 56.2 ± 0.3 | 48.5 ± 0.3 |
| cortex | 52.4 ± 0.3 | 45.3 ± 0.3 |
| midbrain | 49.4 ± 0.4 | 44.1 ± 0.5 |

FIGS. 3A and 3B. MR images (T2, TR 6000 ms, TE 10-120 ms, 12 echoes) of a second 1-year-old rat that is a genetic model of AD (triple genetic model of Aβ plaques) are shown. FIG. 3A shows the baseline (pre-contrast) MR image of a representative slice in this rat. FIG. 3B shows the post-contrast MR image of the same slice, 2.5 hours after injection with the contrast. Comparison of the T2 values of the volumetric ROIs (hippocampus, cortex, and midbrain) in the baseline (FIG. 3A) and post-contrast (FIG. 3B) scans showed significant (P<0.05) contrast enhancement in all ROIs following injection with DNP-MNP. Contrast enhancement was most prominent in the hippocampus, followed by the cortex.

Table 3 shows the quantitative T2 values ("Base T2 (ms)") of the ROIs (hippocampus, cortex, and midbrain) in the baseline scan. Table 3 shows the quantitative T2 values ("Post T2") of the same ROIs in the same rat 2.5 hours after i.v. (tail vein) injection of HODDNP-MNPs.

TABLE 3

| ROI | Base T2 (ms) | Post T2 |
|---|---|---|
| hippocampus | 65.8 ± 0.4 | 51.8 ± 0.4 |
| cortex | 61.0 ± 0.4 | 48.8 ± 0.3 |
| midbrain | 61.0 ± 0.5 | 46.5 ± 0.5 |

FIGS. 4A-C. A representative MRI slice of a transgenic rat model of AD is shown in FIG. 4A. The corresponding boxed area (hippocampus) is shown on a stained histological section in FIG. 4B. The inset shows prominent plaque presence in the hippocampus. More diffuse plaque presence (FIG. 4C) was observed in all brain areas. These results confirm that contrast enhancement with HODDNP-MNPs occurs in the presence of β-amyloid plaques, which are associated with AD.

FIGS. 5A-D. Diffuse plaque presence is shown (FIG. 5A) in the hippocampus. Perl's iron stain in adjacent slices shows the presence of DNP-MNPs in areas containing plaques (FIGS. 5B-D).

FIGS. 6A and 6B. DAB-enhanced Perl's stain of the transgenic rat brain slice (post DNP-MNP intravenous injection, via tail vein) is shown in FIG. 6A. DNP-MNP crossed the BBB and is present in the intracellular (arrows) as well as extracellular brain tissue. DAB-enhanced Perl's stain of the naïve control animal (without contrast injection) (FIG. 6B) shows no iron staining present in the same brain area (entorhinal cortex) shown in FIG. 6A.

Figure 7:
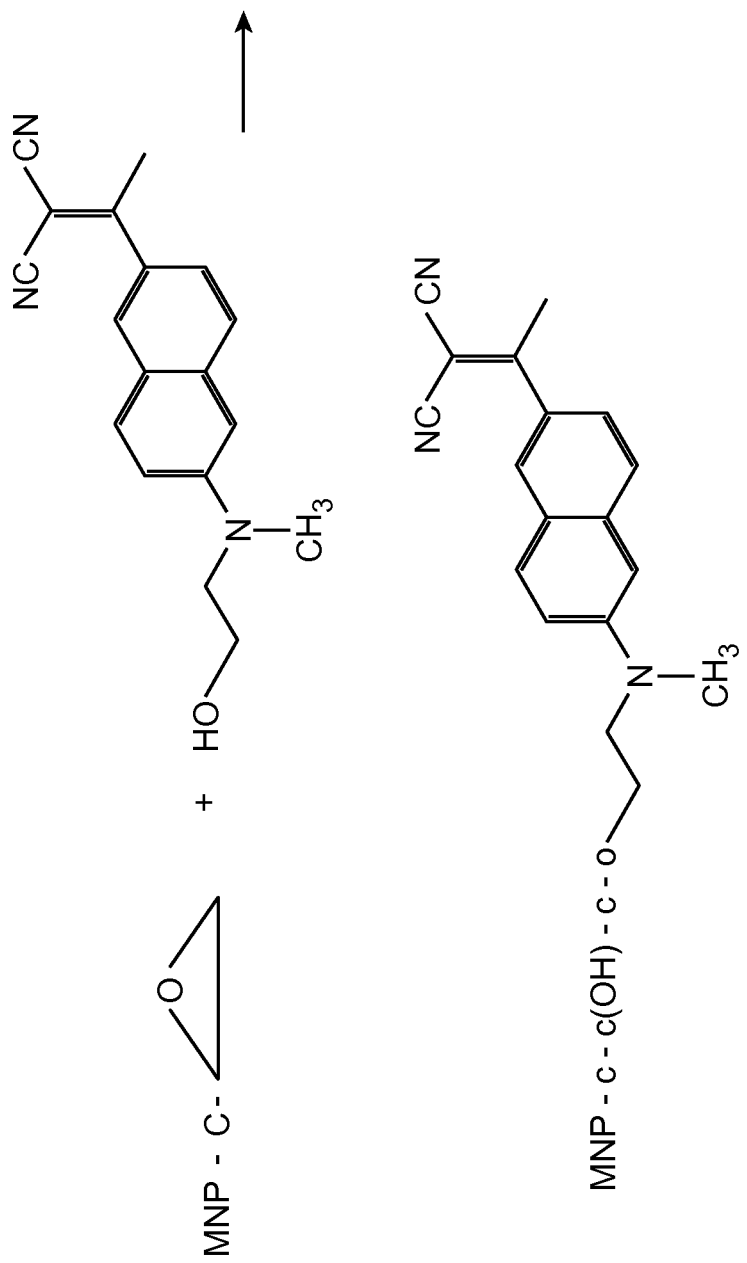
FIG. 7 depicts a method of conjugating 2-(1-{6-[(2-hydroxyethyl)(methyl)amino]-2-naphthyl}ethylidene)malononitrile (HODDNP) to a magnetic nanoparticle.

HODDNP can be covalently conjugated to epoxy-MNPs via the hydroxyl group of HODDNP. An example of a conjugation method is depicted in FIG. 7. PIB-2-conjugated MNPs PIB-2 can be covalently conjugated to epoxy-MNPs via the amino nitrogen of PIB-2. An example of such a method is depicted in FIG. 8.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A pharmaceutical composition comprising:
    a) a functionalized magnetic nanoparticle (MNP) comprising a magnetic core and a functional group that binds aggregated β-amyloid protein and/or neurofibrillary tangles, wherein said functional group is coupled via an epoxy group to the magnetic core, wherein said functionalized magnetic nanoparticle is capable, when introduced into the bloodstream of a mammalian subject, of crossing the blood-brain barrier of a mammalian subject, and wherein the functional group is 2-(1-{6-[(2-hydroxyethyl)(methy)amino]-2-naphthyl}ethylidene) malononitrile(HODDNP), or a derivative or analog thereof; and
    b) a pharmaceutically acceptable carrier.

2. The pharmaceutical composition of claim 1, wherein the HODDNP functional group is coupled to the magnetic core via the hydroxyl group of HODDNP.

3. The pharmaceutical composition of claim 1, wherein the functionalized MNP further comprises a therapeutic agent.

4. The pharmaceutical composition of claim 1, wherein the functionalized MNP is encapsulated in an albumin matrix.

5. The pharmaceutical composition of claim 1, wherein the functionalized MNP comprises an apolipoprotein.

6. The pharmaceutical composition of claim 1, wherein the functionalized MNP comprises poly(butyl cyanoacrylate) (PBCA).

7. The pharmaceutical composition of claim 6, wherein the functionalized MNP is attached to the surface of a PBCA particle.

8. The pharmaceutical composition of claim 1, wherein the functionalized MNP comprises a surfactant.

9. The pharmaceutical composition of claim 8, wherein the surfactant is selected from polyoxyethylene sorbitan monooleate, polyoxyethylene sorbitan monopalmitate, polyoxyethylene sorbitan monostearate, and polyoxyethylene sorbitan monolaurate.

10. The pharmaceutical composition of claim 8, wherein the surfactant is a block copolymer of polyethylene oxide and polypropylene oxide.

11. The pharmaceutical composition of claim 8, wherein the functionalized MNP comprises a poloxamine.

* * * * *